United States Patent
Sawyer et al.

(10) Patent No.: US 11,377,634 B2
(45) Date of Patent: Jul. 5, 2022

(54) 3D MICRO FABRICATION AND SCREENING

(71) Applicant: University of Florida Research Foundation, Inc., Gainesville, FL (US)

(72) Inventors: Wallace Gregory Sawyer, Gainesville, FL (US); Thomas Ettor Angelini, Gainesville, FL (US); Steven C. Ghivizzani, Gainesville, FL (US); C. Parker Gibbs, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 517 days.

(21) Appl. No.: 16/347,701

(22) PCT Filed: Nov. 7, 2017

(86) PCT No.: PCT/US2017/060361
§ 371 (c)(1),
(2) Date: May 6, 2019

(87) PCT Pub. No.: WO2018/085823
PCT Pub. Date: May 11, 2018

(65) Prior Publication Data
US 2019/0270962 A1 Sep. 5, 2019

Related U.S. Application Data

(60) Provisional application No. 62/418,589, filed on Nov. 7, 2016.

(51) Int. Cl.
*C12N 5/00* (2006.01)
*G01N 33/50* (2006.01)
*G06T 7/00* (2017.01)

(52) U.S. Cl.
CPC ......... *C12N 5/0062* (2013.01); *C12N 5/0018* (2013.01); *C12N 5/0068* (2013.01); *G01N 33/5008* (2013.01); *G06T 7/0012* (2013.01); *C12N 2521/00* (2013.01)

(58) Field of Classification Search
CPC .................................................. C12N 5/0018
See application file for complete search history.

(56) References Cited

U.S. PATENT DOCUMENTS

| | | |
|---|---|---|
| 2006/0154852 A1 | 7/2006 | Boden et al. |
| 2010/0234304 A1 | 9/2010 | Boden et al. |
| 2012/0272347 A1 | 10/2012 | Zhang et al. |
| 2013/0012457 A1 | 1/2013 | Boden et al. |
| 2014/0044649 A1 | 2/2014 | Boden et al. |
| 2014/0186273 A1 | 7/2014 | Moradian-oldak et al. |
| 2017/0007737 A1 | 1/2017 | Moradian-oldak et al. |

FOREIGN PATENT DOCUMENTS

| | | |
|---|---|---|
| WO | 00/06108 A1 | 2/2000 |
| WO | 02/094204 A1 | 11/2002 |
| WO | 2004/007532 A1 | 1/2004 |
| WO | 2010/042754 A2 | 4/2010 |
| WO | 2014/027012 A1 | 2/2014 |
| WO | 2016130953 A1 | 8/2016 |
| WO | 2017/123986 A1 | 7/2017 |

OTHER PUBLICATIONS

Gurski et al., Biomaterials, 2009, 30:6076-6085.*
International Search Report issued for PCT/US2017/060361, dated Jan. 30, 2018.
Alkilzy, M., et al., "Treatment of Carious Lesions Using Self-Assembling Peptides," Advances in Dental Research, vol. 29, No. 1 (2018), pp. 42-47.
Barbosa-Martins, Luiz Filipe, et al., "Enhancing bond strength on demineralized dentin by pre-treatment with selective remineralising agents," Journal of Mechanical Behaviour of Biomedical Materials, vol. 81, pp. 214-221.
Braga, Mariana M., et al., "Detection Activity Assessment and Diagnosis of Dental Caries Lesions," Dent. Clin. N. Am., vol. 54 (2010), pp. 479-493.
Brunton, P.A., et al., "Treatment of early caries lesions using biomimetic self-assembling peptides—a clinical safety trial," British Dental Journal, vol. 215, E6 (2013) (6 pages).
Burke, F.J.T., et al., "The ultimate guide to restoration longevity in England and Wales. Part 3: Glass ionomer restorations—time to next intervention and to extraction of the restored tooth," British Dental Journal (2018), pp. 865-874.
Chu, C.H., et al., "A review of sodium fluoride varnish," Gen. Dent. vol. 54, No. 4 (2006), pp. 247-253.
Dikmen, Benin, ICDAS II Criteria (International Caries Detection and Assessment System), J. Istanbul Univ. Fac. Dent., vol. 49, No. 3 (2015), pp. 63-72.
Ekstrand, KR, et al., "Detection and Activity Assessment of Primary Coronal Caries Lesions: A Methodologic Study," Operative Dentistry, vol. 32-3 (2007), pp. 225-235.
Griffin, S.O., et al., "The Effectiveness of Sealants in Managing Caries Lesions," J. Dent. Res., vol. 87, No. 2 (2008), pp. 169-174.
Hepdeniz, Ozge Kam, et al., "The effect of surface sealants with different filler content on microleakage of Class V resin composite restorations," European Journal of Denistry, Sep. 23, 2019 (7 pages).
Kind, L., et al., "Biomimetic Remineralization of Carious Lesions by Self-Assembling Peptide," Journal of Dental Research, vol. 96, No. 7 (2017), pp. 790-797.
Kirkham, J., et al., "Self-assembling Peptide Scaffolds Promote Enamel Remineralization," Journal of Dental Research, vol. 86, No. 10 (2007), pp. 426-430.
Mousavinasab, Sayed Mostafa, et al., "Fluoride Release by Glass Ionomer Cements, Compomer and Giomer," Dent. Res. J., vol. 6, No. 2 (2009), pp. 75.81.
Naaman, Reem, et al., "The Use of Pit and Fissure Sealants—A Literature Review," Dentistry Journal, vol. 5, No. 34 (2017), (19 pages).

(Continued)

Primary Examiner — Bin Shen
(74) Attorney, Agent, or Firm — Thomas | Horstemeyer LLP

(57) ABSTRACT

Disclosed herein is an integrated assay system that can be used, for example, to monitor and screen cells in 3D culture. This system involves a 3D cell growth medium made from a yield stress material that allows cells to be deposited, e.g. by 3D printing, samples to be taken, and the extracellular environment manipulated.

19 Claims, 7 Drawing Sheets

(56) References Cited

OTHER PUBLICATIONS

Nedeljkovic, Ivana, et al., "Is secondary caries with composites a material-based problem?" Dental Materials, vol. 3I (2015), pp. e247-e277.

Nyvad, Bente, et al., "Nyvad Criteria for Caries Lesion Activity and Severity Assessment: A Validated Approach for Clinical Management and Research," Caries Res., vol. 52 (2018), pp. 397-405.

Ruan, Qichao, et al., "An armelogenin-chitosan matrix promotes assembly of an enamal-like layer with a dense interface," Acta Biomaterialia, vol. 9 (2013), pp. 7389-7297.

Ruan, Qichao, et al., "Development of Amelogenin-chitosan Hydrogel for In Vitro Enamel Regrowth with a Dense Interface," Journal of Visualized Experiments, vol. 89 (2014) (10 pages).

Schmidlin, Patrick et al., In vitro re-hardening of artificial enamel caries lesions using enamel matrix proteins or self-assembling peptides, J. Appl. Oral Sci., vol. 24 (2016), pp. 31-36.

Sidhu, Sharanbir K., et al., "A Review of Glass-Ionomer Cements for Clinical Dentistry," Journal of Functional Biomaterials, vol. 7, No. 16 (2016), (15 pages).

Watson, Timothy F., et al., "Present and future of glass-ionomers and calcium-silicate cements as bioactive materials in dentistry: Biophotonics-based interfacial analyses in health and disease," Dental Materials, No. 30 (2014), pp. 50-61.

* cited by examiner

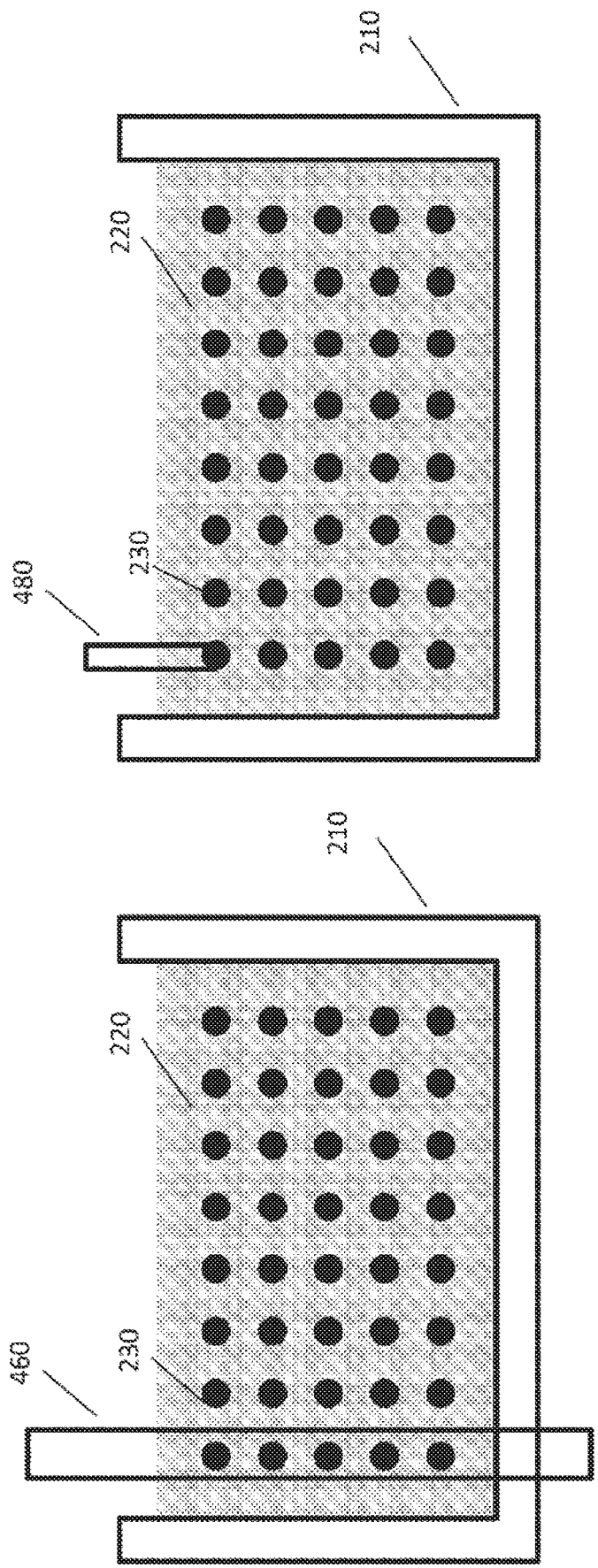

3D MICRO FABRICATION AND SCREENING

CROSS-REFERENCE TO RELATED APPLICATIONS

This application claims benefit of U.S. Provisional Application No. 62/418,589, filed Nov. 7, 2016, which is hereby incorporated herein by reference in its entirety.

TECHNICAL FIELD

Disclosed embodiments are related to growth media for three-dimensional cell culture microfabrication and screening.

BACKGROUND

Conventional cell culture techniques involve growing cells on a two-dimensional (2D) substrate, such as a microwell plate or a Petri dish. Such 2D cell cultures often include a growth medium disposed on the substrate to promote cell growth. However, the 2D environment of conventional cell cultures is often a poor substitute for the three-dimensional (3D) environment experienced by cells in vivo. For example, the behavior of a cell is often highly dependent on the microenvironment around the cell; in a 2D cell culture the microenvironment around the cell may be different than what a cell would experience in a 3D microenvironment.

Several techniques have been developed for 3D cell culture, including the use of hanging drop plates, magnetic levitation, or biomaterial scaffolds. However, these techniques are typically expensive and/or time consuming, and may be limited in the specific structures or geometries of tissues which may be grown and/or tested.

SUMMARY

Disclosed herein is an integrated assay system that can be used, for example, to monitor and screen cells in 3D culture. This system involves a 3D cell growth medium made from a yield stress material that allows cells to be deposited, e.g. by 3D printing, samples to be taken, and the cell environment manipulated. In some cases, this involves a solid to liquid phase change at a desired location in a region of yield stress material such that the yield stress material will flow and be displaced when cells are injected or otherwise placed at the desired location. Once completed, it then transforms back into a solid-like phase to support the printed cells maintain the printed geometry.

The disclosed assay system may include a 3D printer platform and mechanisms to create differentiated growth conditions at different locations within a vessel of the 3D printer. The assay system may further include measurement apparatus to measure characteristics at specific locations within the vessel. The characteristics may be of cells or the medium, including of pharmaceutics introduced into the medium or enzymes or other molecules or compounds secreted by cells growing in the medium.

In some embodiments the assay system may further include bioreactor plates. In some embodiments, the assay system may include one or more standardized cell lines. Correlation between growth of these cell lines in the 3D printer and in vitro may be determined and used to correlate results from measuring conditions with the 3D printer vessel. Such correlations may also be used to determine and control the size, shape and location of groups of cells within the 3D printer vessel.

In some embodiments, the assay system my further include qualified reagents, operating procedures and/or protocols. In addition, quantitative imaging systems and microfluidics handling devices may be included for the assessment and/or segregation of spheroids for expansion or in depth analyses as well as systems for the controlled spatial and temporal delivery of soluble drugs and reagents Also disclosed is a method of using the disclosed assay system that involves first providing a three-dimensional (3D) cell growth medium comprising a plurality of hydrogel particles and a liquid cell culture medium, wherein the hydrogel particles are swelled with the liquid cell culture medium to form a granular gel.

The method can then involve depositing one or more cells into the granular gel. For example, the cells can be deposited in a pattern within the granular gel. This can involve, for example, arranging the cells in a predefined geometry within the three-dimensional cell growth medium. In some embodiments, the predefined geometry is at least one of a spheroid, an embryoid body, a tumor, or cyst. In some cases, the pattern comprises at least one region surrounded by the granular gel such that cells growing in the region experience a pressure that is less than a yield stress of the granular gel. In some embodiments, more than one cell type is used, creating a microtissue within the 3D medium. In some embodiments, the cells are deposited into the granular gel in a series of discrete wells. For example, the granular gel can be in a well plate, such as a 24, 48, or 96 well plate.

The method can then involve culturing the cells (e.g. microtissue) for a first period of time. Standard cell culture methods can be used for this step. For example, the culture can be placed in an incubator that controls temperature and atmospheric gases. The duration of the culture can vary depending on the cell type(s) and purpose. Non-limiting examples of candidate agents that can be evaluated by this system include a polypeptide, polynucleotide, carbohydrate, organic molecule, inorganic molecule, or any hybrid or combination thereof.

In some embodiments, a candidate agent is present in the 3D growth medium during the first period of time, and the duration of this first period of time is an amount sufficient to give the candidate agent time to have a detectable effect on the cells. In some cases, the candidate agent is administered locally by injection into the granular gel. In other cases, the candidate agent diffuses through the 3D medium. In some cases, the candidate agent is administered to a circulatory system present in the microtissue.

In some embodiments, the cells are exposed to a stimulus before or during the first period of time, and the duration of the first period of time is an amount sufficient to give the stimulus time to have a detectable effect on the cells. For example, the stimulus can be an electromagnetic radiation, sound waves, electrical stimulation, mechanical force, temperature change, atmospheric gas change, atmospheric pressure change, or any combination thereof.

The method can then involve collecting a first sample from the granular gel. The sample can then be analyzed to evaluate potential changes in the cells or the microenvironment, e.g. as a result of the candidate agent and/or stimulus. In some cases, the sample is a cell sample. For example, a cell sample can be analyzed for protein expression, nucleic acid expression, or a combination thereof. In some cases, the sample is a sample of an extracellular microenvironment. For example a cell extracellular microenvironment can be analyzed for presence of a protein, nucleic acid, carbohydrate, or any hybrid or combination thereof. The sample can also be analyzed for the presence of a drug or drug metabolite.

The method can then involves culturing the cells (e.g. microtissue) for a second period of time for additional evaluation. This is an advantage of the disclosed system as samples can be taken without disrupting 3D geometry of the cells.

This process can be repeated multiple times, e.g. collecting a second sample from the granular gel, culturing the cells, collecting a third sample, etc. . . .

The method can further involve imaging the cells before, during or after the first period of time, the second period of time, or a combination thereof. For example, the cells can be imaged continuously during the first period of time, the second period of time, or a combination thereof.

In some embodiments, the three-dimensional cell growth medium has a yield stress such that the cell growth medium undergoes a phase change from a first solid phase to a second liquid phase upon application of a shear stress greater than the yield stress. For example, the yield stress can be on the order of 10 Pa+/−25%. In some cases, the concentration of hydrogel particles is between 0.05% to about 1.0% by weight. In some embodiments, the hydrogel particles have a size in the range of about 0.1 μm to about 100 μm when swollen with the liquid cell culture medium. In some cases, the hydrogel particles have a size in the range of about 1 μm to about 10 μm when swollen with the liquid cell culture medium.

In some embodiments, there are molecules diffused into the granular gel particles and throughout the granular gel. For example, the molecules can be small molecules or proteins. In some cases, the molecules are small molecules, and wherein the small molecules comprise nutrients or dissolved gasses.

The details of one or more embodiments of the invention are set forth in the accompanying drawings and the description below. Other features, objects, and advantages of the invention will be apparent from the description and drawings, and from the claims.

DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIGS. 4A-4D illustrate examples of an apparatus for imaging a 3D cell culture.

DETAILED DESCRIPTION

Figure 1:
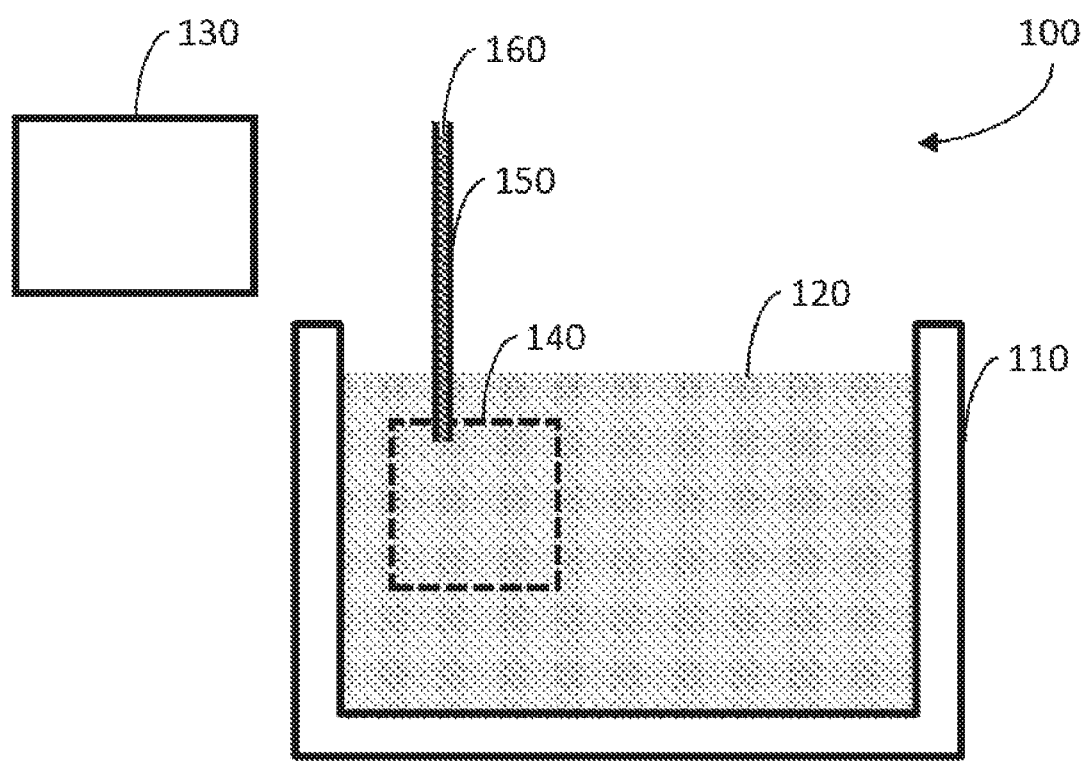
FIG. 1 is a schematic representation of one embodiment of an apparatus for placing cells in a 3D cell growth medium.

Disclosed herein is a 3D cell growth medium that allows for easy placement and/or retrieval of groups of cells, which may enable rapid and/or high throughput testing. Such testing may reduce or eliminate the need for pre-clinical animal testing as part of new drug development. For example, these techniques allow cells to be grown in structures that mimic the dynamic environment of a tissue or tumor. Drugs may be applied to microtissues such that an indication of the efficacy of such drugs can be obtained in a fashion that is more reliable than using conventional in vitro test techniques.

For example, a microtissue can be produced using a combination of parenchymal cells, mesenchymal cells, immune cells, and vasculature forming cells.

In some cases, the cells are tumor cells. In these embodiments, additional cells can be deposited with the tumor cells, representing the tissue in which they can be found.

Any type of agent can be screened using this system. For example, a candidate agent can be a polypeptide, polynucleotide, carbohydrate, organic molecule, inorganic molecule, or any hybrid or combination thereof. For example, the candidate agent can be an antibody. The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

In some embodiments, the candidate agent is a cell. Therapeutic cells are known in the art and include stem cells, progenitor cells, and immune cell. The cells can be isolated cells, cell lines, or engineered cells (e.g. CAR-T cells).

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof.

Other stimuli can also be evaluated to determine positive and negative effects on microtissues. For example, the stimulus can be an electromagnetic radiation, chemical stimulus, osmotic stimulation, sound waves, electrical stimulation, mechanical force, temperature change, atmospheric gas change, atmospheric pressure change, or any combination thereof.

The effect of these agents and stimuli on microtissues can be evaluated from a sample collected from the 3D culture without disrupting the 3D geometry.

In some cases, the sample is a cell sample. For example, a cell sample can be analyzed for gene expression, protein production and/or localization, cell activity/function, or combinations thereof. In some embodiments, the cell is analyzed by an immunoassay. Examples of immunoassays are enzyme linked immunosorbent assays (ELISAs), radio-immunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP). In some embodiments, the cell is assayed by using a gene expression assay. Examples of gene expression assays include Northern blot, RNAse protection assay, reverse transcription (RT)-PCR, real-time PCR (qPCR), in-situ hybridization, dot-blot analysis, differential display, subtractive hybridization, DNA microarrays, RNA microarrays, NANOSTRING, and second generation sequencing (NGS).

In some cases, the sample is of an extracellular microenvironment. For example the extracellular microenvironment can be analyzed for presence of a protein, nucleic acid, lipid, carbohydrate, or any hybrid or combination thereof. In some embodiments, the extracellular microenvironment is analyzed for pH, gases, salts, or other such physical, biological, and/or chemical properties.

The sample can also be analyzed for the presence of a drug or drug metabolite. In particular, the sample can be analyzed for any agent or metabolite thereof added to the system.

In some embodiments, the method involves injecting something into the granular gel, e.g. dosing a substance, instead of, or in addition to, taking a sample. In some embodiments, the method involves removing material, such as waste, from the extracellular microenvironment. Again, the disclosed system has the advantage of allowing such manipulations without disrupting the 3D geometry.

The method can further involve imaging the cells before, during or after the first period of time, the second period of time, or a combination thereof. For example, the cells can be imaged continuously during the first period of time, the second period of time, or a combination thereof. In some embodiments, the system comprises a computer capable of analyzing the images and tracking the cells in the culture. This can be useful in evaluating, for example, cell growth, motility, interaction, etc. . . . In addition, cell tracking can be used to automate other steps in the method, such as sample collection. In some cases, sample collection is automated by the computer, which tracks the cell locations and takes a sample from the culture based on cell position.

The cells can also be monitored for luminescence, fluorescence, absorption, or radiation, e.g. to detect probes or imaging agents. The cells can also be monitored by magnetic resonance imaging, computed tomography, x-ray imaging, or ultrasound.

In some embodiments, the disclosed 3D cell growth medium comprises hydrogel particles dispersed in a liquid cell growth medium. In some embodiments, any suitable liquid cell growth medium may be used; a particular liquid cell growth medium may be chosen depending on the types of cells which are to be placed within the 3D cell growth medium. Suitable cell growth medium may be human cell growth medium, murine cell growth medium, bovine cell growth medium or any other suitable cell growth medium. Depending on the particular embodiment, hydrogel particles and liquid cell growth medium may be combined in any suitable combination. For example, in some embodiments, a 3D cell growth medium comprise approximately 0.5% to 1% hydrogel particles by weight. In accordance with some embodiments, the hydrogel particles may be made from a bio-compatible polymer.

In some embodiments, the hydrogel particles swell with the liquid growth medium to form a granular gel material. Depending on the particular embodiment, the swollen hydrogel particles may have a characteristic size at the micron or submicron scales. For example, in some embodiments, the swollen hydrogel particles may have a size between about 0.1 µm and 100 µm. Furthermore, a 3D cell growth medium may have any suitable combination of mechanical properties, and in some embodiments, the mechanical properties may be tuned via the relative concentration of hydrogel particles and liquid cell growth medium. For example, a higher concentration of hydrogel particles may result in a 3D growth medium having a higher elastic modulus and/or a higher yield stress.

Such tunability may be advantageous for controlling the environment around a group of cells placed in a 3D cell growth medium. For example, a 3D cell growth medium may have mechanical properties which are tuned to be similar to those found in vivo so that the cells 3D growth medium may emulate the natural environment of the cells. However it should be understood that the mechanical properties of a 3D cell growth medium may not be similar to those found in vivo, or may be tuned to any suitable values, as the disclosure is not so limited.

According to some embodiments, a 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

The disclosed 3D cell growth medium made from a yield stress material allows for facile placement and/or retrieval of a group cells at any desired location within the 3D growth medium. For example, placement of cells may be achieved by causing a solid to liquid phase change at a desired location in a region of yield stress material such that the yield stress material will flow and be displaced when cells are injected or otherwise placed at the desired location. After injection, the yield stress material may solidify around the placed cells, and therefore trap the cells at the desired location.

However, it should be appreciated that any suitable techniques may be used to deposit cells or other biological materials within the 3D growth medium. For example, using a syringe, pipette or other suitable tool, cells may be injected into one or more locations in the 3-D growth medium. In some embodiments, the injected cells may be shaped as a pellet, such as by centrifugation. However, it should be appreciated that a 3D growth medium as described herein enables injection of cells suspended in a liquid, which may avoid a centrifugation step in conducting tests.

Regardless of how cells are placed in the medium, the yield stress of the yield stress material may be large enough to prevent yielding due to gravitational and/or diffusional forces exerted by the cells such that the position of the cells within the 3D growth medium may remain substantially constant over time. Since the cells are fixed in place, they may be retrieved from the same location at a later time for assaying or testing by causing a phase change in the yield stress material and removing the cells. As described in more detail below, placement and/or retrieval of groups of cells may be done manually or automatically.

A yield stress material as described herein may have any suitable mechanical properties. For example, in some embodiments, a yield stress material may have an elastic modulus between of approximately 0.1 Pa to 1000 Pa (including 0.1 to 10 Pa; 1.0 to 10 Pa; 0.1 to 50 Pa; 1.0 to 50 Pa; 0.1 to 100 Pa; 1.0 to 100 Pa; 10 to 100 Pa; 100 to 500 Pa; or 500 to 1000 Pa) when in a solid phase or other phase in which the material retains its shape under applied stresses at levels below the yield stress. In some embodiments, the yield stress required to transform a yield stress material to a fluid-like phase may be between approximately 0.01 Pa and 1000 Pa (including 0.1 to 10 Pa; 1.0 to 10 Pa; 0.1 to 50 Pa; 1.0 to 50 Pa; 0.1 to 100 Pa; 1.0 to 100 Pa; 10 to 100 Pa; 100 to 500 Pa; or 500 to 1000 Pa). When transformed to a fluid-like phase, a yield stress material may have a viscosity between approximately 0.01 Pa s and 10,000 Pa s (including 0.1 to 10 Pa s; 1.0 to 10 Pa s; 1.0 to 100 Pa s; 10 to 100 Pa s; 10 to 1,000 Pa s; 100 to 1,000 Pa s; 100 to 10,000 Pa s; 1,000 to 10,000 Pa s; or 5,000 to 10,000 Pa s). However, it should be understood that other values for the elastic modulus, yield stress, and/or viscosity of a yield stress material are also possible, as the present disclosure is not so limited.

In some embodiments, the yield stress may be tuned to match the compressive stress experienced by cell groups in vivo, as described above. Without wishing to be bound by any particular theory, a yield stress material which yields at a well-defined stress value may allow indefinite and/or unrestricted growth or expansion of a group of cells. Specifically, as the group of cells grows, it may exert a hydrostatic pressure on the surrounding yield stress material; this hydrostatic stress may be sufficient to cause yielding of the yield stress material, thereby permitting expansion of the group of cells. In such embodiments, the yielding of the yield stress material during growth of a group of cells may result in the yield stress material maintaining a constant pressure on the group of cells during growth. Moreover, because a yield stress material will yield when an applied stress exceeds the yield stress, a 3D growth medium made from a yield stress material may not be able to apply a stress to a group of cells which exceeds the yield stress. Such an upper bound on the stress applied to a group of cells may help to ensure that cells are not unnaturally constrained, damaged or otherwise altered due to the application of large compressive stresses.

According to some embodiments, a 3D growth medium made from a yield stress material may yield to accommodate excretions such as fluids or other extracellular materials from a group of cells disposed within the 3D growth medium. Without wishing to be bound by any particular theory, excretion of fluids or other materials from a group of cells may result in an increase in the pressure in the extracellular space; if the pressure exceeds the yield stress of the 3D growth medium, the 3D growth medium may yield to accommodate the excretions, and a group of cells may excrete fluids or other materials without restriction. Such an ability of a 3D growth medium to accommodate cellular excretion may allow the 3D growth medium to more closely match an in vivo environment. Moreover, a 3D growth medium made from a yield stress material may allow for facile removal of cellular excretions for assaying, testing, or any other suitable purpose, as described in more detail below.

A group of cells may be placed in a 3D growth medium made from a yield stress material via any suitable method. For example, in some embodiments, cells may be injected or otherwise placed at a particular location within the 3D growth medium with a syringe, pipette, or other suitable placement or injection device. In some embodiments an array of automated cell dispensers may be used to inject multiple cell samples into a container of 3-D growth medium. Movement of the tip of a placement device through the 3D growth medium may impart a sufficient amount of energy into a region around the tip to cause yielding such that the placement tool may be easily moved to any location within the 3D growth medium. In some instances, a pressure applied by a placement tool to deposit a group of cells within the 3D growth medium may also be sufficient to cause yielding such that the 3D growth medium flows to accommodate the group of cells. Movement of a placement tool may be performed manually (e.g. "by hand"), or may performed by a machine or any other suitable mechanism.

In some embodiments, multiple independent groups of cells may be placed within a single volume of a 3D cell growth medium. For example, a volume of 3D cell growth medium may be large enough to accommodate at least 2, at least 5, at least 10, at least 20, at least 50, at least 100, at least 1000, or any other suitable number of independent groups of cells. Alternatively, a volume of 3D cell growth medium may only have one group of cells. Furthermore, it should be understood that a group of cells may comprise any suitable number of cells, and that the cells may of one or more different types.

Depending on the particular embodiment, groups of cells may be placed within a 3D cell growth medium according to any suitable shape, geometry, and/or pattern. For example, independent groups of cells may be deposited as spheroids, and the spheroids may be arranged on a 3D grid, or any other suitable 3D pattern. The independent spheroids may all comprise approximately the same number of cells and be approximately the same size, or alternatively different spheroids may have different numbers of cells and different sizes. In some embodiments, cells may be arranged in shapes such as embryoid or organoid bodies, tubes, cylinders, toroids, hierarchically branched vessel networks, high aspect ratio objects, thin closed shells, or other complex shapes which may correspond to geometries of tissues, vessels or other biological structures. Regardless of the shape, in some embodiments, the 3D printing techniques as described herein may be used to produce groups of cells with repeatable shapes.

According to some embodiments, a 3D cell growth medium made from a yield stress material may enable 3D printing of cells to form a desired pattern in three dimensions. For example, a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells. After injection, the 3D cell growth medium may transform back into a solid-like phase to support the printed cells and maintain the printed geometry. However, it should be understood that 3D printing techniques are not required to use a 3D growth medium as described herein.

A 3D cell growth medium made from a yield stress material may also allow for facile retrieval of groups of cells from within the cell growth medium via a reversal of the steps used to deposit the cells. For example, cells may be removed by simply moving a tip of a removal device such as a syringe or pipette to a location where a group of cells is disposed, and applying suction to draw the cells from the cell growth medium. As described above, movement of the tip of the removal device through the 3D cell growth medium may impart sufficient energy to the material to cause yielding and accommodate removal of the cells from the 3D cell growth medium. Such an approach may be used, for example, as part of a test process in which multiple cell samples are deposited in 3D growth medium. Those deposited cells may be cultured under the same conditions, but different ones of the samples may be exposed to different drugs or other treatment conditions. One or more samples may be harvested at different times to test impact of the treatment conditions on the cells.

In some embodiments in which cells excrete fluids or other materials into an extracellular space, the excretions may be removed from the cell growth medium with similar methods while not removing the cells. For example, the 3D cell growth medium may support the cells and keep them substantially stationary when removing cellular excretions. In some embodiments, yielded 3D cell growth medium may flow to fill in space which was previously occupied by removed cells and/or cellular excretions.

In some embodiments, a 3D cell growth medium may be used to support and/or preserve the structure of a cell-laden engineered tissue construct. For example, a tissue construct including a scaffold or other suitable structure on which a plurality of cells is disposed may be placed into a 3D cell culture medium. The 3D cell culture medium may provide support to preserve a complex structure of the tissue construct while also providing a 3D environment for cell growth which may mimic that found in vivo.

According to some embodiments, a 3D cell growth medium may be prepared by dispersing hydrogel particles in a liquid cell growth medium. The hydrogel particles may be mixed with the liquid cell growth medium using a centrifugal mixer, a shaker, or any other suitable mixing device. During mixing, the hydrogel particles may swell with the liquid cell growth medium to form a material which is substantially solid when an applied shear stress is below a yield stress, as discussed above. After mixing, entrained air or gas bubbles introduced during the mixing process may be removed via centrifugation, agitation, or any other suitable method to remove bubbles from 3D cell growth medium.

In some embodiments, preparation of a 3D cell growth medium may also involve buffering to adjust the pH of a hydrogel particle and liquid cell growth medium mixture to a desired value. For example, some hydrogel particles may be made from polymers having a predominantly negative charge which may cause a cell growth medium to be overly acidic (have a pH which is below a desired value). The pH of the cell growth medium may be adjusted by adding a strong base to neutralize the acid and raise the pH to reach the desired value. Alternatively, a mixture may have a pH that is higher than a desired value; the pH of such a mixture may be lowered by adding a strong acid. According to some embodiments, the desired pH value may be in the range of about 7.0 to 7.4, or, in some embodiments 7.2 to 7.6, or any other suitable pH value which may, or may not, correspond to in vivo conditions. The pH value, for example may be approximately 7.4. In some embodiments, the pH may be adjusted once the dissolved $CO_2$ levels are adjusted to a desired value, such as approximately 5%

In one non-limiting example, a 3D cell growth medium comprises approximately 0.2% to about 0.7% by mass Carbopol particles (Lubrizol). The Carbopol particles are mixed with and swell with any suitable liquid cell growth medium, as described above, to form a 3D cell growth medium which comprises approximately 99.3% to about 99.8% by mass cell growth medium. After swelling, the particles have a characteristic size of about 1 μm to about 10 μm. The pH of the mixture is adjusted to a value of about 7.4 by adding a strong base, such as NaOH. The resulting 3D cell growth medium is a solid with a modulus of approximately 100-300 Pa, and a yield stress of approximately 20 Pa. When a stress is applied to this 3D cell growth medium which exceeds this yield stress, the cell growth medium transforms to a liquid-like phase with a viscosity of approximately 1 Pa s to about 1000 Pa s. As described above, the specific mechanical properties may be adjusted or tuned by varying the concentration of Carbopol. For example, 3D cell growth media with higher concentrations of Carbopol may be stiffer and/or have a larger yield stress. Additionally, one or more polymers, such as polylysine, may be mixed with the 3D cell growth medium to at least partially neutralize the negative charge of the granular gel material. The concentration of the one or more polymers may be between 1 and 100 micrograms per milliliter.

The terms "yield stress" and "yield stress material" have been used and characterized in different ways in the art. For ease of description herein, unless indicated otherwise, the terms "yield stress" and "yield stress material" should be understood to be a Herschel-Bulkley yield stress determined using the Herschel-Bulkley equation $$\sigma = \sigma_y + k\dot{\gamma}^p$$

where $\sigma_y$ is yield stress, $\sigma$ is shear stress, k is viscosity index of the material, $\dot{\gamma}$ is shear rate, and p is a positive number, and a material having such a yield stress.

In addition, "yield stress" (i.e., Herschel-Bulkley yield stress) has been measured in different ways in the art. Unless indicated otherwise herein, a yield stress of a sample is determined by shearing the sample in a rheometer using plate-plate geometry and via the Herschel-Bulkley equation, via the following process. Prior to shearing, the rheometer tool surfaces may be roughened to prevent or mitigate slipping at the sample-tool interface. Using the rheometer, the sample is sheared at a variety of shear rates, extending from high shear rates (e.g., 1000 $s^{-1}$) to low shear rates (0.001 $s^{-1}$). For each shear rate, the sample is sheared for 30 seconds, after which shear stress data is collected and averaged. A series of shear stress measurements are collected sequentially for each shear rate. These shear rates are then used, via the Herschel-Bulkley equation, to determine (1) whether the material has a yield stress (i.e., a Herschel-Bulkley yield stress), and (2) the yield stress for the material. Those skilled in the art will appreciate that, for a material having a yield stress, a plot of shear stress versus shear rate will exhibit a plateau region at low shear rates, with the data points asymptotically approaching the material's yield stress at low shear rates. The yield stress is the shear stress at these low, near-zero shear rates, or an estimate of shear stress at zero strain rate determined using a low or near-zero shear rate, such as a shear rate of $10^{-3}$ $s^{-1}$. As used herein (unless indicated otherwise), a "yield stress material" will be a material that has a yield stress determinable via this process. Those skilled in the art will appreciate that for a yield stress material (i.e., a Herschel-Bulkley yield stress material) at low shear (e.g., a near-zero shear rate), a shear stress is independent of shear rate and instead exhibits only a shear stress dependent only on an elastic component of the material.

Turning now to the figures, specific non-limiting embodiments of 3D cell growth media and methods for their preparation and/or use are described in more detail.

FIG. 1 depicts a schematic representation of one embodiment of an apparatus 100 for placing groups of cells in a 3D cell growth medium 120. The apparatus 100 may include a container 110, a focused energy source 130, and an injector 150. The container 110 may hold the 3D cell growth medium 120. The focused energy source 130 may cause a phase change in a region 140 of the 3D cell growth medium 120 by applying focused energy to the region 140. The injector 150 may displace the 3D cell growth medium 120 with a material 160 which may include a plurality of cells.

According to some embodiments, the container 110 may be a tub, a bowl, a box, or any other suitable container for the 3D cell growth medium 120. As described above, the 3D cell growth medium 120 may include a thixotropic or yield stress material, or any material suitable for temporary phase changing. Additionally, the cell growth medium 120 may include extracellular matrix proteins, such as collagen or laminin, to improve cell function and more accurately recreate in vivo behavior. In some examples, the thixotropic or yield stress material may include a soft granular gel. The soft granular gel may be made from polymeric hydrogel particles swelled with a liquid cell culture medium. Depending on the particular embodiment, the hydrogel particles may be between 0.5 µm and 50 µm in diameter, between about 1 µm and 10 µm in diameter, or about 5 µm in diameter when swelled.

Figure 2B:
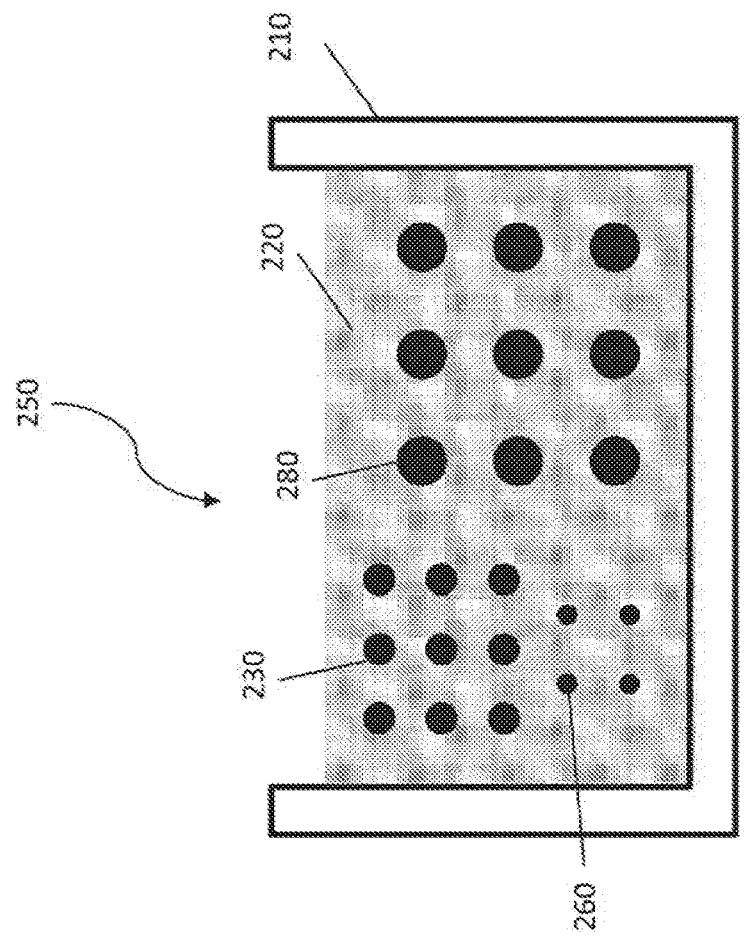
FIGS. 2A-2D are schematic representations of embodiments of a 3D cell growth medium including a plurality of cell spheroids.
Figure 2A:
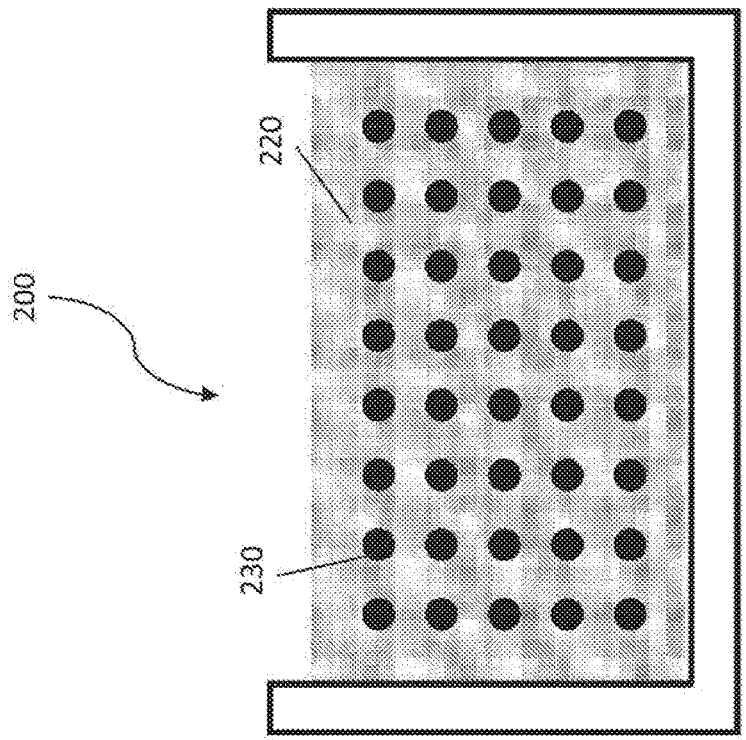

FIG. 2A depicts a cross sectional view of one embodiment of a 3D cell culture 200 including a 3D cell growth medium 220 disposed in a container 210. A plurality of spheroids 230 comprising one or more cells is arranged in the 3D cell growth medium 220. In the depicted embodiment, the spheroids 230 are approximately the same size and are spaced evenly spaced apart. In some embodiments, the spheroids may not all have the same size and/or spacing. For example, the FIG. 2B depicts another embodiment of a 3D cell culture 250 including small spheroids 260, intermediately sized spheroids 270, and large spheroids 280. In view of the above, it should be understood that cells spheroids of cells may have any suitable combination of sizes and/or spacing. Although spheroids are depicted, it should be understood that groups of cells may not be spheroid, and may be embryoid, organoid, toxoid, or have any other suitable shape, as the disclosure is not so limited.

Figure 2C:
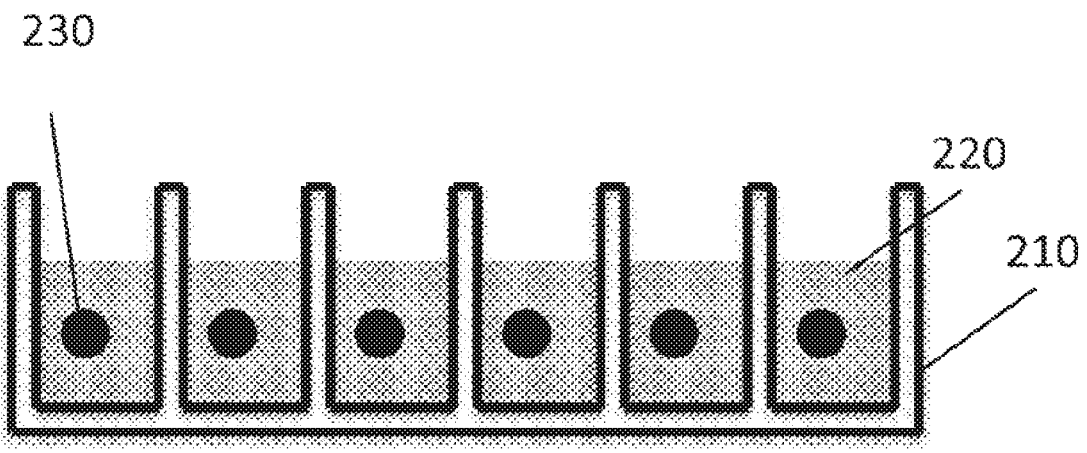
Figure 2D:
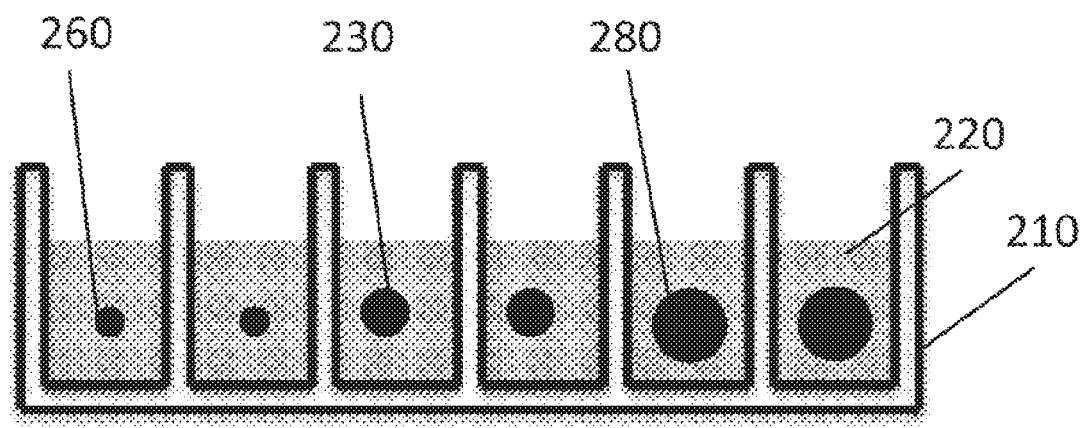

FIGS. 2A and 2B Figures illustrate the generation of multiple cell clusters, here shown as spheres, in the same vessel. FIGS. 2C and 2D illustrate the generation of multiple identical spheres or spheres of various sizes in numerous individual vessels. Vessels as illustrated may be formed in a tray 210 or other suitable carrier to facilitate high throughput testing. However, it should be appreciated, that any suitable vessel or vessels may be used.

Regardless of the type of vessel used, once the cells are deposited, the medium containing the cells may be incubated in diverse environments which may alter its chemical properties and in turn modify the growth environment of the 3D cultures contained within. For example, cells in the medium may be incubated in low oxygen or hypoxic environments.

It should be appreciated that one or more compounds may be deposited in conjunction with and/or adjacent to cells. For example, soluble, non-cellular components could be deposited in conjunction with the cells. These might include structural proteins (e.g. collagens, laminins), signaling molecules (growth factors, cytokines, chemokines, peptides), chemical compounds (pharmacologic agents), nucleic acids (e.g. DNA, RNAs), and others (nano-particles, viruses, vectors for gene transfer). It should be understood that the embodiments of 3D cell growth media described herein are not limited to any particular types of cells. For example, various embodiments of 3D cell growth media may be used with animal, bacterial, plant, insect, or any other suitable types of cells.

Figure 3B:
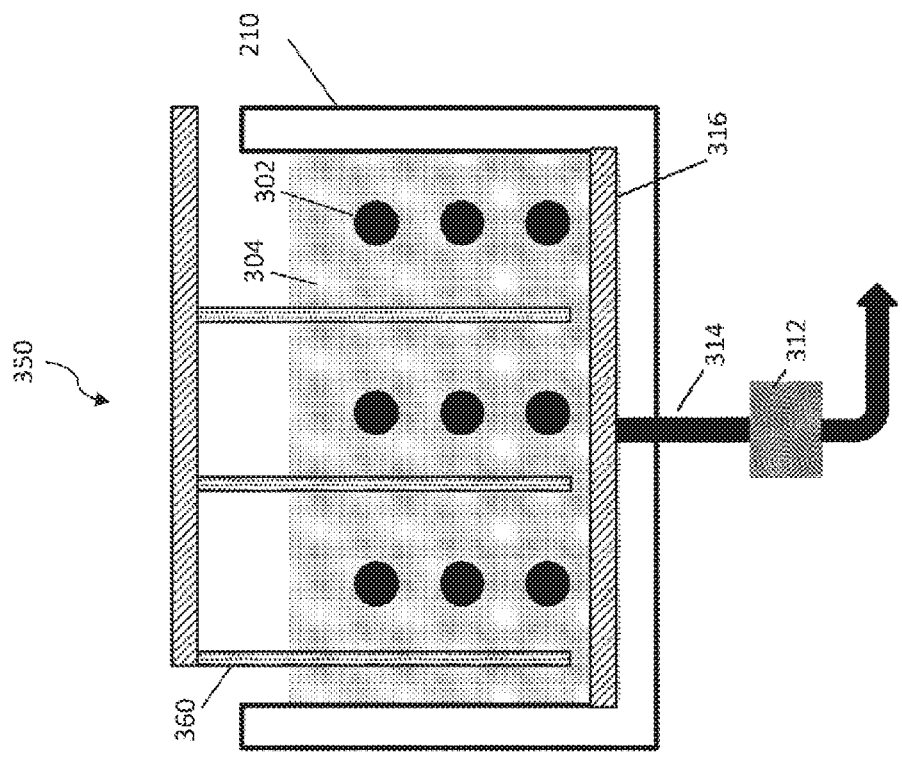
FIGS. 3A-3B illustrate examples of an apparatus for culturing and interacting with a 3D cell culture.
Figure 3A:
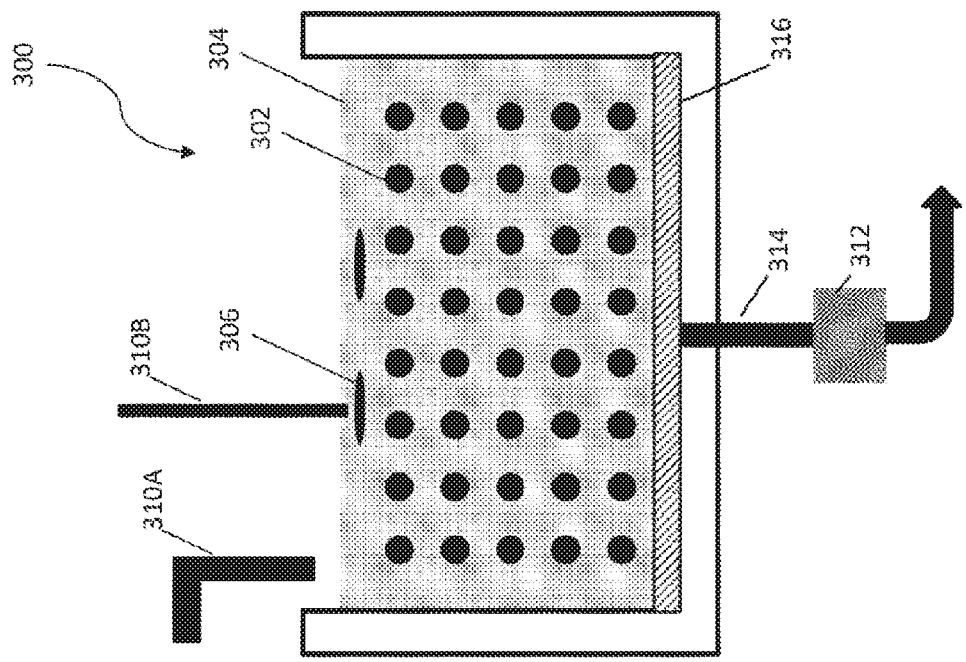

FIGS. 3A-3B illustrate examples of a cell culture and interaction apparatus, including examples of interaction equipment of such an apparatus.

FIG. 3A illustrates an apparatus 300 in which biological cells 302 are suspended at specific locations within a 3D cell growth medium 304. The apparatus includes interaction equipment 310A and 310B to dispense material into the 3D cell growth medium 304. Equipment 310A may dispense a cell growth material that, when combined with a hydrogel, forms the 3D cell growth material 304. The equipment 310A may dispense the cell growth material to supply nutrients as cells 302 absorb and use the cell growth material from the 3D cell growth material 304. Equipment 310B may also dispense material, such as by dispensing drug-loaded controlled release materials 306 into the 3D cell growth material 304. The controlled release materials 306 may diffuse through the 3D cell growth medium 304 to be absorbed by the cells 302.

Apparatus 300 may further include interaction equipment to remove fluids from the 3D cell growth material 304. As illustrated in FIG. 3A, the apparatus 300 may include a pump (e.g., a vacuum pump) 312, which may draw fluids out of the 3D cell growth material 304 via an outflow 314. In some embodiments, as illustrated in FIG. 3A, the apparatus 300 may include a filter-like membrane 316, which may permit some materials to pass into the outflow 314 but may block a hydrogel of the 3D cell growth material 304 or other materials from passing.

FIG. 3B illustrates another example of an apparatus 350, including different interaction equipment. Equipment and materials of the example of FIG. 3B that are the same as equipment/materials of FIG. 3A share the same reference numbers. The example of FIG. 3B illustrates perfusion tubing 360 to permit dispensing of one or more materials into the 3D cell growth material 304. Three perfusion tubes are illustrated. The same materials may be dispensed from each tube 360, or different materials may be dispensed. The materials that may be dispensed include a cell growth material, pharmaceuticals, or other compounds.

The equipment 310B and 360 of the examples of FIGS. 3A and 3B may be operated, in some embodiments, to dispense materials at particular locations within the 3D cell growth medium 304 and, in some embodiments, may be operated to dispense materials to form a concentration gradient of the materials across the 3D cell growth medium 304. By forming a gradient, different cells 302 may be exposed to different concentrations of a material. Following exposure, the cells 302 may be inspected (within or outside of the 3D cell growth medium 304) to determine an impact of different concentrations of the materials on the cells 302.

In some embodiments, as discussed above, the equipment 310B and 360 of FIGS. 3A and 3B may be dynamically inserted and removed from the 3D cell growth medium 304, while the cells 302 are cultured in the 3D cell growth medium 304.

In the examples of FIGS. 3A and 3B, the pump 312 may be used to remove materials from the 3D cell growth medium 304 for any suitable purpose. For example, the pump 312 may be operated to remove a byproduct of cellular activity, including waste generated by the cells or a protein or other byproduct of cellular activity that is to be harvested. As another example, the pump 312 may impose a force on the 3D cell growth medium 304 so as to draw materials (e.g., materials dispensed by equipment 310A, 310B, 360) through the 3D cell growth medium 304. While a pump 312 is shown applying such a force in the examples of FIGS. 3A and 3B, in other embodiments the source of the force may be a centrifuge spinning the apparatus 300, 350, or gravity, or any other suitable source of a force.

Figures 4C, 4D:
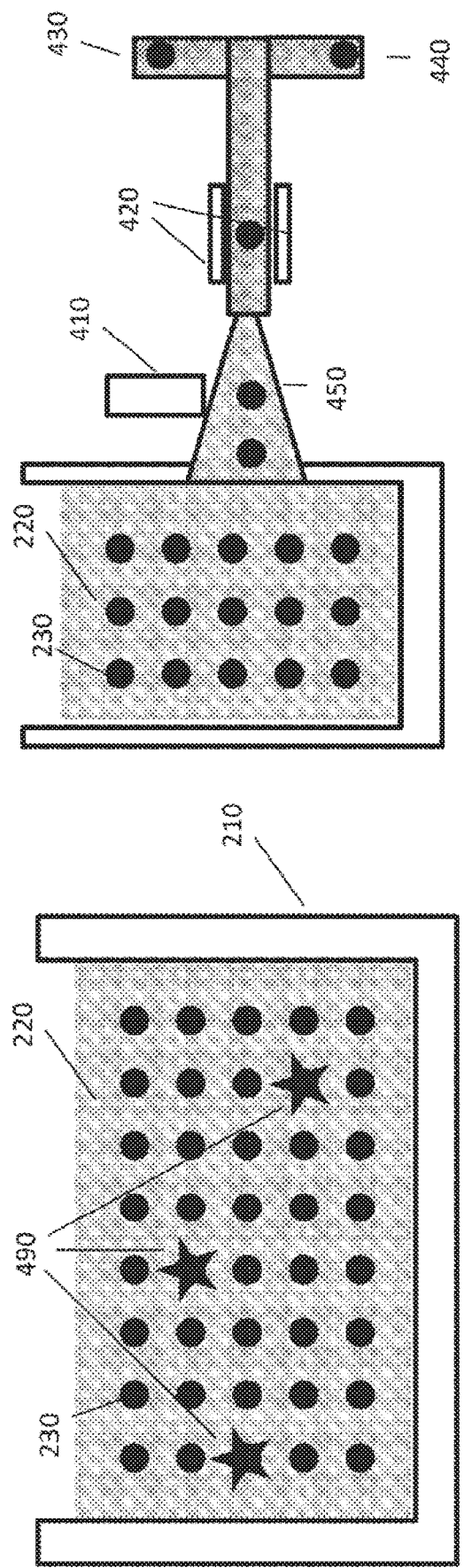

FIGS. 4A-4D illustrate examples of an apparatus for imaging a 3D cell culture. Numerous imaging and detection systems for optical readouts (e.g. luciferase, green, red, yellow fluorescent proteins) may aid in visualization and rapid, quantitative assessment of tumor spheres and their temporal responses to treatment. Reagent tumor lines may bear transcriptional reporters reflecting tumorigenic potential that may include genetically encoded optical sensors of intracellular calcium levels representing changes in stress, metabolic activity, activation of apoptotic pathways and secreted proteins. FIGS. 4A-4B illustrate laser based fluorescence imaging. In FIG. 4A, spheroids 230, such as tumor spheres, within the growth medium 220 may be irradiated by a laser sheet 460, or any planar laser configuration. Spheroids irradiated by the sheet may fluoresce to signal a state from the reporters within the spheroids. Fluorescent gene reporters may signal for malignant potential or adaptive differentiation, among other traits. The laser sheet 460 may irradiate any plane within the container 210 and the laser sheet 460 may be sourced from any suitable optical source for fluorescence imaging. In FIG. 4B, the laser 480 is targeted to irradiate the spheroids 2230 individually. In FIG. 4C, the spheroids 230 may contain fluorescent gene reporters that fluoresce or induce fluorescence in the visible spectrum without external stimulation. The spheroids 490 are represented by stars to indicate that they are fluorescing.

In accordance with some embodiments, the location at which fluorescence is detected may be correlated to one or more experimental variables. By depositing groups of cells in specific locations, using techniques as described herein in which the groups of cells maintain their locations, detected fluorescence in a particular location may be associated with a specific group of cells. Groups of cells may be formed differently and each group of cells may be tracked over time. For example groups of cells may be formed with different sizes such that response of a cell group of different size to different conditions might be studied by observing luminescence at different locations. Such an approach may be used to calibrate growth characteristics within a 3D printer to growth in vivo under similar conditions. Alternatively or additionally, such an approach may be used to simultaneously test reaction to cell groups of different characteristics to the same conditions created with the 3D printer vessel.

Alternatively or additionally, the cell groups at different locations throughout the 3D printer vessel may be exposed to different conditions, such as, for example, drugs of different concentrations, enabling simultaneous testing of reaction to different conditions. By correlating conditions at a location to where fluorescence is detected, specific conditions producing a reaction in cell groups may be determined.

Other imaging techniques may occur outside of the container 210, but may nonetheless in some embodiments be performed so as to measure conditions and/or cell reactions at specific locations within the 3D printer vessel. In FIG. 4D fluorescence-activated cell sorting is illustrated. Spheroids 230 may go through a sheath 450 where they may be individually detected by a detector 410, which may measure a characteristic of the spheroids 230 such as fluorescence. Once detected, the spheroids 230 may pass through biasing elements 420 to sort them into two or more distinct groups 430 and 440. The groups may be based off of a characteristic of the spheroids 230 such as charge, if the biasing elements 420 use electrostatic deflection. In other embodiments, a different sorting mechanism, such as mechanically opening or closing valves or other flow passages, may be used, or no sorting mechanism may be used if only the results from the detector 410 are desired.

In the embodiment illustrated in FIG. 4, an outlet of the 3D printer vessel is in a fixed location. In other embodiments, the outlet may be movable and may be computer controlled similarly to the injector tip. The outlet may be moved through the vessel in a controlled pattern such that, at different, but known times, cells in different regions of the vessel are drawn into the outlet. In this, at controlled times, cells from different regions of the vessel, which may have been exposed to different conditions may be drawn into a sample chamber for analysis. Accordingly, the time of a detected signal measured in the sample chamber may be correlated to cells exposed to a specific set of growth conditions.

Figure 5:
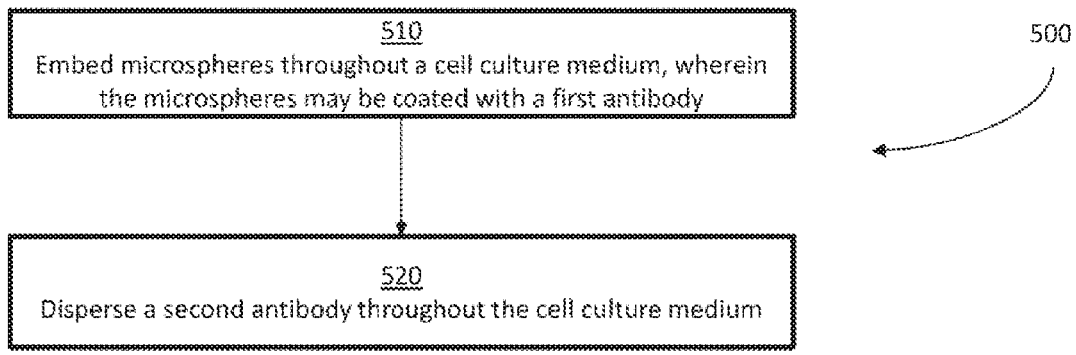
FIG. 5 is a flowchart of a method for preparing a 3D cell culture for an enzyme-linked immunosorbent assay test.

Other techniques may be used to detect properties of cells while in the 3D printing vessel, FIG. 5 is a flowchart of a method for preparing a 3D cell culture for an enzyme-linked immunosorbent assay test. In act 510, microspheres may be embedded throughout a growth medium, such as the one shown in FIG. 2. The microspheres may be coated with a first antibody. In act 520, one or more second antibodies may be dispersed throughout the cell culture medium. The reaction of the first antibody and second antibody may produce a detectable signal, such as emitted light or based on a change in a response to light or other energy. In some embodiments, the microspheres may be positioned in the growth medium with a 3D printing vessel such that enzymes may be detected at particular locations with the growth medium. Those locations may be selected based on proximity to groups of cells or in any other suitable way. The ordering of the acts should not be considered a limitation, in other embodiments the acts may occur in a different order.

Figure 6:
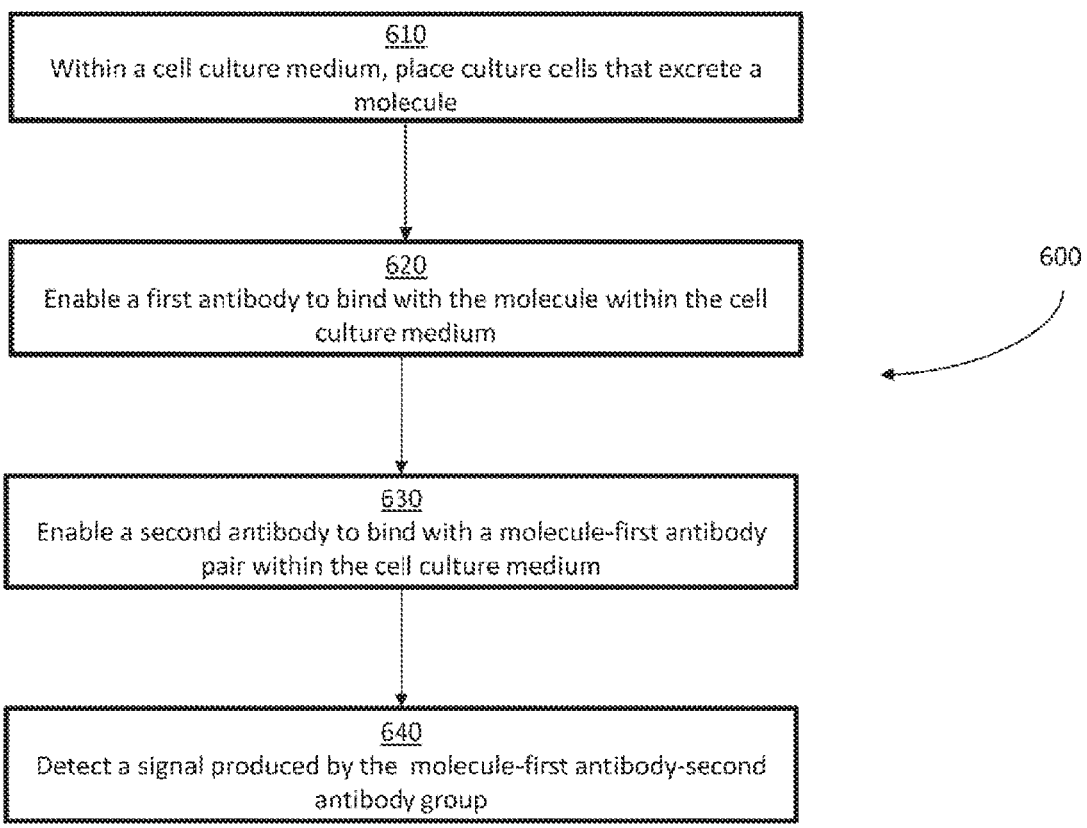
FIG. 6 is a flowchart of a method for a 3D cell culture undergoing an enzyme-linked immunosorbent assay test.

FIG. 6 is a flowchart of a method for a 3D cell culture undergoing an enzyme-linked immunosorbent assay test. In act 610, one or more cells may be placed within the cell culture medium and may excrete one or more molecules. In act 620, the one or more molecules may be enabled to bind to one or more of the first antibodies coating one or more microspheres within the cell culture medium, as described above, to create a molecule-first antibody pair. In act 630, one or more second antibodies, as described above, may be enabled to bind to one or more of the molecule-first antibody pairs to create one or more molecule-first antibody-second antibody groups. In act 640 a detectable signal, such as fluorescence, may be detected from one or more of the molecule-first antibody-second antibody groups. The signal may indicate tumor response to drug testing, or other factors. The order of the acts should not be considered limiting, and only serve to illustrate one embodiment. In another embodiment, for example, act 630 may occur before act 620, the one or more second antibodies may be enabled to bind to the one or more first antibodies creating one or more first antibody-second antibody pairs to which the one or more excreted molecules may bind. As the one or more first antibodies are coated over one or more microspheres within the growth medium, the signals generated by the test may emanate from one or more known locations within the growth medium, increasing detection efficiency.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method, comprising
   (a) providing a three-dimensional (3D) cell growth medium comprising a plurality of hydrogel particles and a liquid cell culture medium, wherein the hydrogel particles are swelled with the liquid cell culture medium to form a granular gel, wherein the 3D cell growth medium has a yield stress such that the cell growth medium undergoes a phase change from a solid phase to a liquid phase upon application of a shear stress greater than the yield stress, wherein the yield stress is 1 to 100 Pa;
   (b) depositing one or more cells into the granular gel with a depositing device by applying a first shear stress greater than the yield stress of the 3D cell growth medium to change the 3D cell growth medium into a liquid phase, wherein after the cells are deposited and the shear stress is removed, the 3D cell growth medium fills in space created by the depositing device before changing to a solid phase and trapping the cells at the desired location;
   (c) culturing the cells for a first period of time;
   (d) collecting a first sample from the granular gel with a collection device by applying a second shear stress greater than the yield stress of the 3D cell growth medium to change the 3D cell growth medium into a liquid phase, wherein after the first sample is collected and the shear stress is removed, the 3D cell growth medium fills in space created by the collection device before changing to a solid phase;
   (e) culturing the cells for a second period of time;
   (f) repeating step (d) to collect a second sample; and
   (g) analyzing the first sample, the second sample, or a combination thereof, to evaluate changes in the cells or the extracellular environment.

2. The method of claim 1, wherein the first sample, the second sample, or a combination thereof is a cell sample, wherein the cell sample is analyzed for protein expression, nucleic acid expression, or a combination thereof.

3. The method of claim 1, wherein the first sample, the second sample, or a combination thereof is a sample of an extracellular environment, wherein the extracellular environment is analyzed for presence of a protein, nucleic acid, carbohydrate, or any hybrid or combination thereof.

4. The method of claim 1, wherein a candidate agent is present in the 3D growth medium during the first period of time, the second period of time, or a combination thereof, wherein the first sample, the second sample, or a combination thereof is collected to evaluate the effect of the candidate agent on the cells.

5. The method of claim 4, wherein the candidate agent is selected from a polypeptide, polynucleotide, carbohydrate, organic molecule, inorganic molecule, or any hybrid or combination thereof.

6. The method of claim 1, further comprising exposing the cells to a stimulus.

7. The method of claim 6, wherein the stimulus is selected from electromagnetic radiation, sound waves, electrical stimulation, mechanical force, temperature change, atmospheric gas change, atmospheric pressure change, or any combination thereof.

8. The method of claim 1, further comprising imaging the cells before, during or after the first period of time, the second period of time, or a combination thereof.

9. The method of claim 8, wherein the cells are imaged continuously during the first period of time, the second period of time, or a combination thereof, wherein the position of the cells is tracked by a computer based on the cell image.

10. The method of claim 9, wherein collection of the first sample, the second sample, or a combination thereof is automated by the computer.

11. The method of claim 1, wherein the cells are deposited in a pattern within the granular gel, wherein depositing the cells comprises arranging the cells in a predefined geometry within the three-dimensional cell growth medium, wherein the predefined geometry is at least one of a spheroid, an embryoid body, a tumor, or cyst.

12. The method of claim 11, wherein the pattern comprises at least one region surrounded by the granular gel such that cells growing in the region experience a pressure that is less than a yield stress of the granular gel.

13. The method of claim 1, wherein the yield stress is on the order of 10 Pa+/−25%.

14. The method of claim 1, wherein the concentration of hydrogel particles is between 0.05% to about 1.0% by weight.

15. The method of claim 1, wherein the hydrogel particles have a size in the range of about 0.1 μm to about 100 μm when swollen with the liquid cell culture medium.

16. The method of 15, wherein the hydrogel particles have a size in the range of about 1 μm to about 10 μm when swollen with the liquid cell culture medium.

17. The method of claim 1, further comprising molecules diffused into the granular gel particles and throughout the granular gel.

18. The method of claim 17, wherein the molecules comprise small molecules or proteins.

19. The method of claim 18, wherein the molecules are small molecules, and wherein the small molecules comprise nutrients or dissolved gasses.

* * * * *